(12) United States Patent
Andersson et al.

(10) Patent No.: US 6,899,099 B2
(45) Date of Patent: *May 31, 2005

(54) METHOD FOR TREATING A RESPIRATORY DISEASE

(75) Inventors: Bertil Andersson, Bjärred (SE); Thor-Björn Conradsson, Södra Sandby (SE); Göran Eriksson, Dalby (SE)

(73) Assignee: AstraZeneca AB, Södertälji (SE)

( * ) Notice: Subject to any disclaimer, the term of this patent is extended or adjusted under 35 U.S.C. 154(b) by 101 days.

This patent is subject to a terminal disclaimer.

(21) Appl. No.: 10/409,398

(22) Filed: Apr. 7, 2003

(65) Prior Publication Data

US 2003/0192533 A1 Oct. 16, 2003

Related U.S. Application Data

(63) Continuation of application No. 09/220,137, filed on Dec. 23, 1998, now Pat. No. 6,598,603.
(60) Provisional application No. 60/070,291, filed on Dec. 31, 1997.

(51) Int. Cl.$^7$ ............................................. A61M 11/00
(52) U.S. Cl. .............................. 128/200.14; 128/203.12
(58) Field of Search ....................... 128/200.14, 200.23, 128/203.12, 203.15

(56) References Cited

U.S. PATENT DOCUMENTS

| | | | | | |
|---|---|---|---|---|---|
| 4,829,996 | A | * | 5/1989 | Noakes et al. ......... | 128/200.14 |
| 5,049,389 | A | * | 9/1991 | Radhakrishnan ............ | 424/450 |
| 5,510,339 | A | * | 4/1996 | Gleich et al. ................ | 514/171 |
| 5,631,267 | A | * | 5/1997 | Gleich et al. ................ | 514/312 |
| 5,681,584 | A | * | 10/1997 | Savastano et al. .......... | 424/473 |
| 5,688,782 | A | * | 11/1997 | Neale et al. ................ | 514/180 |
| 5,695,744 | A | * | 12/1997 | Neale et al. .................... | 424/45 |
| 5,744,123 | A | * | 4/1998 | Akehurst et al. ............. | 424/45 |
| 5,833,950 | A | * | 11/1998 | Taylor et al. .................. | 424/45 |
| 5,837,713 | A | * | 11/1998 | Gleich ........................ | 514/312 |
| 5,849,265 | A | * | 12/1998 | Li-Bovet et al. .............. | 424/45 |
| 5,875,776 | A | * | 3/1999 | Vaghefi ................. | 128/203.12 |
| 5,894,841 | A | * | 4/1999 | Voges .................... | 128/200.14 |
| 5,906,202 | A | * | 5/1999 | Schuster et al. ....... | 128/203.12 |
| 5,955,439 | A | * | 9/1999 | Green ......................... | 514/23 |
| 5,957,124 | A | * | 9/1999 | Lloyd et al. ........... | 128/200.14 |
| 5,971,951 | A | * | 10/1999 | Ruskewicz ............. | 128/200.14 |
| 5,972,919 | A | * | 10/1999 | Carling et al. .............. | 514/171 |
| 5,996,576 | A | * | 12/1999 | Yule ...................... | 128/203.12 |
| 6,013,245 | A | * | 1/2000 | Taylor et al. .................. | 424/45 |
| 6,014,969 | A | * | 1/2000 | Lloyd et al. ........... | 128/200.14 |
| 6,070,575 | A | * | 6/2000 | Gonda et al. .......... | 128/203.12 |
| 6,126,919 | A | * | 10/2000 | Stefely et al. ................. | 424/45 |
| 6,153,173 | A | * | 11/2000 | Sapsford et al. .............. | 424/45 |
| 6,183,782 | B1 | * | 2/2001 | Hallworth ................... | 424/497 |
| 6,518,239 | B1 | * | 2/2003 | Kuo et al. ...................... | 514/2 |
| 6,598,603 | B1 | * | 7/2003 | Andersson et al. .... | 128/200.24 |
| 6,699,886 | B2 | * | 3/2004 | Parks et al. .................. | 514/340 |
| 2003/0216329 | A1 | * | 11/2003 | Robinson et al. ............. | 514/26 |

OTHER PUBLICATIONS

International Patient Package Leaflet for Pulmicort® suspension for nebulisation 0.125 mg/ml, 0.25 mg/ml and 0.5 mg/ml, ASTRA, approved by Thor–Bjorn Conradson, Aug. 18, 1994 version, pp. 1–8.

Dunn et al., "Inhaled Corticosteroids in Severe Bronchopulmonary Dysplasia (BDP)," No. 1263, Pediatric Research 25 (4 Part 2):213A, 1989.

Dunn et al., "Nebulized Steroids for Bronchopulmonary Dysplasia (BDP)–A Randomised, Double–Blind Cross–Over Study," Pediatr. Res. 31 (4 pt 2):201A, 1992.

Georgitis, "A Study of Once–A –Day Budesonide Nebulizing Suspension (BNS) and Placebo (PBO) in Asthmatic Children Aged Six Months to Eight Years," Chest 112(3):375, Sep. 1997 Supplement.

Goodwin, "An uncontrolled assessment of nebulised budesonide in the treatment of acute infantile bronchiolitis," British Journal of Clinical Research 6:113–119, 1995.

Husby et al., "Treatment of croup with nebulised steroid (budesonide): a double blind, placebo controlled study," Archives of Disease in Childhood 68:352–355, 1993.

Jonasson et al., #P1441 "Clinical efficacy of a low dose inhaled budesonide in children with mild asthma previously not treated with steroids," The European Respiratory Journal 10(25):221s–222s, 1997.

McCarty, "of 'Nebuhaler' and face–mask in young asthmatic children," The Lancet 335:983–984, 1990.

McCarthy, "The use of a once daily inhaled glucocorticosteroid (budesonide) in the management of childhood asthma," British Jounal of Clinical Research 4:55–61, 1993.

Möller et al., #0778 "Administration of Budesonide via Turbuhaler® . . . in Children with Asthma," Eur.Respir.J. 9(23):115s, 1996.

Morice et al., "A comparison of nebulized budesonide with oral prednisolone in the treatment of exacerbations of obstructive pulmonary disease," Clinical Pharmacology & Therapeutics 60:675–678, 1996.

Pearlman, P42 "HPA–Axis function in Asthmatic Infants & Young Children Treated with Budesonide Nebulizing Suspension (BNS) or Placebo (PBO) Once–A–Day (QD)," Annual Meeting ACAAI, San Diego, CA (USA) Nov. 7–12, 1997.

Reijonen et al., "Anti–inflammatory Therapy Reduces Wheezing After Branchiolitis," Arch Pediatr. Adolesc. Med. 150:512–517, 1996.

(Continued)

Primary Examiner—Aaron J. Lewis
(74) Attorney, Agent, or Firm—Fish & Richardson P.C.

(57) ABSTRACT

The invention provides a novel method of treating respiratory diseases, e.g., pediatric asthma, in a continuing regimen with not more than one daily dose of the drug budesonide using a nebulizer.

27 Claims, No Drawings

OTHER PUBLICATIONS

Takao et al., "Effects of Inhaled Nebulized Steroids (Budesonide) on Acute and Chronic Lung Function in Heart–Lung Transplant Patients," Transplantation Proceedings 27:1284–1285, 1995.

Weiner et al., "Long term clinical comparison of single versus twice daily administration of inhaled budesonide in moderate asthma," Thorax 50:1270–1273, 1995.

de Blic et al., "Efficacy of neubulized budesonide in treatment of severe infantile asthma: A double–blind study", J. Allergy Clin. Immunol. 98:14–20, 1996.

Godrey et al., "Nebulised Budesonide in Severe Infantile Asthma", The Lancet, II:851–852, 1987.

Grimfeld, "Long–term Study of Nebulised Budesonide in Young Children With Moderate to Severe Asthma", Eur. Resp. J., 7:27s, 1994.

Ijangovan et al., "Treatment of severe steroid dependent preschool asthma with nebulised budesonide suspension", Archives of Disease in Childhood, 68:356–359, 1993.

Vikre–Jorgensen et al., "Dose Titration of Nebulized Budesonide in Young Children", Pediatric Pulmonology, 23:270–277, 1997.

Pedersen et al., "Budesonide suspension for nebulisation in children with asthma", Eur. Respir. J., 2(Suppl. 8):647S, 1989.

Volovitz et al., "Rapid induction of clinical response with a short–term high–dose starting schedule of budesonide nebulizing suspension in young children with recurrent wheezing episodes", J. Allergy Clin. Immunol. 101:464–469, 1998.

Wennergren et al., "Nebulized budesonide for the treatment of moderate to severe asthma in infants and toddlers", Acta Paediatr, 85:183–189, 1996.

* cited by examiner

METHOD FOR TREATING A RESPIRATORY DISEASE

This application in a continuation of U.S. application Ser. No. 09/220,137, filed Dec. 23, 1998, now U.S. Pat. No. 6,598,603, which claims benefit of U.S. Provisional Application Ser. No. 60/070,291, filed Dec. 31, 1997. The disclosures of U.S. application Ser. No. 09/220,137 and U.S. Provisional Application No. 60/070,291 are incorporated herein by reference in their entirety.

BACKGROUND OF THE INVENTION

The invention relates to the treatment of respiratory diseases.

There is significant difficulty in the treatment of young children, including infants, who suffer from respiratory diseases, e.g., asthma. In light of the requirement for frequent and repeated administration of appropriate drugs, issues of compliance and convenience are major aspects of this problem. Furthermore, current methods of intrapulmonary delivery of drugs, e.g., glucocorticosteroids (GCS), are not optimal for use in infants and young children.

SUMMARY OF THE INVENTION

The invention provides a new method of treating respiratory diseases such as asthma that involves administering a budesonide composition with a nebulizer not more than once per day. This administration regimen improves compliance and convenience, both significant factors in treating these diseases, particularly in infants and young children. Moreover, the nebulizer is readily and effectively used with infants as well as young children.

Specifically, the invention features a method of treating a patient suffering from a respiratory disease in which a composition, e.g., a suspension, of budesonide is administered by nebulization at a frequency of between once per day and once per month in a continuing regimen. For example, the frequency of administration can be once and only once per day, or once and only once every two days. The doses can be, e.g., 0.05 mg to 15 mg, 0.1 mg to 2.0 mg, or 0.25 mg to 1.0 mg budesonide. The drug can be provided as an aqueous suspension in which the budesonide is suspended in a solvent containing about 0.05 mg to 0.15 mg sodium edetate, about 8.0 mg to 9.0 mg sodium chloride, about 0.15 mg to 0.25 mg polysorbate, about 0.25 mg to 0.30 mg anhydrous citric acid, and about 0.45 mg to 0.55 mg sodium citrate per 1 ml of water.

This new method of treatment can be used in patients suffering from respiratory diseases that include, for example, inflammatory airway diseases, croup, and bronchopulmonary dysplasia. Inflammatory airway diseases include asthma, chronic obstructive pulmonary disease (COPD), and bronchiolitis. Patients can be any age from birth, e.g., newborn, one day to fifteen years old, one month to eight years old, or six months to five years old. The method is also effective in older patients.

A "continuing regimen," is a treatment regimen of a series of two or more administrations that occur over days, weeks, months, or years. The dosage of each administration can be the same or varied throughout the continuing regimen.

The doses of budesonide specified for administration by nebulization are those added to the nebulizing device. In a typical situation, approximately 40% to 60% of the drug actually leaves the nebulizer, and of this only approximately 25% (i.e., 10% to 15% of the nominal dose) is delivered to the patient. This is because the drug is delivered constantly, and when the patient is exhaling, the drug leaving the nebulizer will not be delivered to the patient; it will instead be lost to the environment. Of the amount delivered to the patient, approximately 6% to 9% of the nominal dose is delivered to the lungs.

The invention also features a kit for treating respiratory diseases, the kit including a budesonide composition in a sealed container, the composition including 0.05 mg to 15 mg budesonide and a solvent, and a label indicating administration by nebulization in a continuing regimen at a frequency of not more than once per day.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents and other references mentioned herein are incorporated by reference in their entirety. In case of conflict, the present specification, including definitions, will control. In addition, the materials, methods, and examples are illustrative only and not intended to be limiting.

Other features and advantages of the invention, e.g., treatment of childhood asthma, will be apparent from the following description and from the claims.

DETAILED DESCRIPTION

The invention is a convenient yet highly effective method of treating asthma involving not more than one administration per day in a continuing dosage regimen. This new method represents a significant advantage, particularly in infants and young children in which it is frequently difficult to achieve compliance with treatments involving more frequent administrations. Such treatments can involve the use of portable propellant-based inhalers which a young child can either use improperly, lose, or be embarrassed to use in front of his or her peers. Once a day or less frequent treatments are cost effective and result in an improved quality of life. In general, a patient (or a patient's family) can choose a time of administration that is convenient for them.

In infants, standard inhalation devices are technically difficult to use. The fact that in the new method the drug can be delivered by a mask applied over the infant's nose and mouth obviates this problem. In addition, in using the nebulizer for administration, the drug is constantly pumped into the face mask. Thus, effective drug delivery does not require constant and deep inhalation. This aspect of the treatment is also advantageous in, for example, incapacitated or neurologically impaired patients.

Two randomized, double-blind, placebo-controlled, twelve-week studies assessed the efficacy and safety of budesonide in children six months to eight years of age who had persistent asthma that was not effectively controlled by non-GCS therapies. The budesonide suspended in a solvent (or a placebo) was administered once per day by a nebulizer connected to a compressor. This treatment resulted in statistically significant improvements in asthma symptoms and a decrease in the number of days in which auxiliary bronchodilator medication was used. Furthermore, there were no significant differences between treatment groups in the type, incidence, or severity of adverse events. There were also no apparent differences between the groups in changes observed in physical examinations, clinical laboratory tests, or oropharyngeal or nasal fungal cultures. Measurement of adrenocorticotropic hormone (ACTH)-induced plasma cortisol levels showed no evidence of hypothalamus-pituitary-adrenal (HPA)-axis suppression by budesonide after twelve weeks of treatment. In summary, these results demonstrated both the efficacy and safety of budesonide when administered to children once per day.

After it has been taken up by airway cells, budesonide forms conjugates (esters) with long-chain fatty acids such as oleic acid. Unlike free budesonide, the budesonide conjugates are inactive as they do not bind to the GCS receptor. However, the conjugation of budesonide is a reversible process. As the concentration of free budesonide in the airway cells falls, the conjugates undergo lipolysis, and further free budesonide is produced, thus maintaining the level available for receptor binding. Intracellular conjugated budesonide thus acts as a "depot" of free budesonide in the airway cells, prolonging the local effect of the compound. This proposed mechanism of action is exemplary; the invention is not limited by any particular mechanism of action.

Methods of Treating Respiratory Diseases

The invention features a new method for treating a patient suffering from a respiratory disease using the drug budesonide which is administered to the patient not more frequently than once per day. It can be delivered, for example, once a day, once every 1.5 days, once every 2 days, once every 3 days, once a week, once every two weeks, or once a month. Treatment is in a continuing regimen for as long as required.

The drug can be delivered dispersed in a solvent, e.g., in the form of a solution or a suspension. It can be suspended in an appropriate physiological solution, e.g., physiological saline or a buffered solution containing 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. The budesonide suspension can made, for example, from micronized budesonide.

The therapeutic suspensions can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres.

The budesonide suspension is provided in a substantially sterile form by, for example, dry-heating the budesonide powder for 2 to 6 hours at 90° C. to 150° C. and employing sterile manufacture for the rest of the process. This involves production and sterilization by filtration of the buffered solvent solution used for the suspension, aseptic suspension of the budesonide in the sterile buffered solvent solution, and dispensing of the suspension into sterile receptacles by methods familiar to those of ordinary skill in the art. This process results in a sterility assurance of 6 as required by the Food and Drug Administration of the U.S. government.

The route of administration is intrapulmonary and the drug is delivered in a nebulized composition by, for example, a nebulizer connected to a compressor (e.g., the Pari LC-Jet Plus® nebulizer connected to a Pari Master® compressor manufactured by Pari Respiratory Equipment, Inc., Richmond, Va.).

Patients are those suffering from a respiratory disease. Relevant respiratory diseases include inflammatory airway diseases, croup, and bronchopulmonary dysplasia. Examples of inflammatory airway diseases include asthma, COPD and bronchiolitis.

Patients can be of either sex. They can be treated by the new method at any age from birth. They can, for example be treated as early as thirty minutes after birth. The patients can also much older, e.g., twelve months, two years, four years, ten years, forty years, or even seventy years of age, or older. Patients can be six months to five or eight years old.

Doses of budesonide can be the same, or can be varied, for patients of all age groups and all sizes and weights. When administered as a nebulized suspension, the dose can be, e.g., 0.05 mg to 15 mg, 0.1 mg to 2.0 mg, or 0.25 mg to 1.0 mg budesonide per administration. Evening administration can result in better control of nocturnal and early morning symptoms which are frequent problems in asthma. If excess budesonide is used in a single administration, it is unlikely that harmful effects will occur.

Nebulizable budesonide is provided, for example, as single dose units (e.g., sealed plastic containers or vials) packed in foil envelopes. Each vial contains a unit dose (e.g., 0.25 mg, 0.5 mg, or 1.0 mg) of micronized budesonide suspended in a volume, e.g., 2 ml, of solvent. The unit dose or, if desired and directed by a physician, a fraction of the unit dose is added to the nebulizer. Patients should rinse out their mouths with water after administration of each dose.

Where diseases other than asthma are to be treated with solvent dispersed budesonide, optimal doses can be established by methods familiar to those in the art, e.g., methods analogous to those described in Examples 1 and 2. Doses, for example, for COPD, bronchiolitis, croup, and bronchopulmonary dysplasia, as in asthma, can generally be 0.05 to 15 mg, 0.1 mg to 2.0 mg, or 0.25 mg to 1.0 mg budesonide per administration.

The following examples are meant to illustrate, not limit, the invention.

EXAMPLES

Example 1

A Phase III Study of Three Dose Levels of Once-A-Day Budesonide Nebulizing Suspension and Placebo in Asthmatic Children Objectives The objectives of the study were to compare the relative efficacy and safety of a nebulizing suspension of budesonide (containing 0.25 mg, 0.5 mg, or 1.0 mg of budesonide per dose), administered once a day, in pediatric asthmatic patients aged six months to eight years.

Methodology

This was a multicenter, randomized double-blind, placebo-controlled, parallel-group study.

Number of Subjects

The total number of patients in the study was 359, the number analyzed for efficacy was 358 and the number analyzed for safety was 359.

Diagnoses and Main Criteria for Inclusion

Patients were asthmatic children who had not been treated with steroids in the 30 days prior to initiation of the study treatment. They were aged six months to eight years of age and had a diagnosis of asthma as defined by the National Institutes of Health of the U.S. Department of Health and Human Services, including: (a) exacerbations of cough and/or wheezing on a frequent basis, including nocturnal asthma, with infrequent severe exacerbations during the last six months; (b) daily use of at least one chronic asthma medication with periodic use of breakthrough medication for at least three months prior to Visit 1; (c) basal $FEV_1$ (forced expiratory volume, in liters per second) of $\geq 50\%$ of predicted, and reversibility of $\geq 15\%$ at $15\pm5$ minutes after a standard dose of inhaled bronchodilator for patients old enough to perform consistent pulmonary function tests (PFT).

Test Drug, Doses, and Mode of Administration

Budesonide was administered once per day as a nebulized suspension, at 0.25 mg, 0.5 mg, or 1.0 mg per administration, via a Pari LC-Jet Plus® nebulizer connected to a Pari Master® compressor (Pari Respiratory Equipment, Inc., Richmond, Va.) with a face mask or a mouth piece. The placebo was the solvent used for the budesonide suspension (0.1 mg disodium edetate, 8.5 mg NaCl, 0.2 mg polysorbate, 0.28 mg anhydrous citric acid, and 0.5 mg sodium citrate per 1 ml water) but without budesonide.

Efficacy Variables

Primary efficacy variables were mean changes from baseline in daytime and nighttime asthma symptom scores over the 12 week treatment phase. The symptom scores are based on the subjective evaluation by the patients or their parents based on a 0–3 rating system in which 0=no symptoms, 1=mild symptoms, 2=moderate symptoms, and 3=severe symptoms.

Secondary efficacy variables were: (a) patient outcomes, including the proportion of patients who were discontinued from the study for any reason and the proportion of patients who were discontinued from this study due to worsening asthma; (b) the number of days breakthrough (bronchodilator) medication was used; (c) spirometry test variables, including $FEV_1$, $FEF_{25-75}$ (forced expiratory flow during the middle half of the forced vital capacity in liters per second) and FVC (forced vital capacity in liters), performed at clinic visits in the subset of patients capable of performing spirometry testing; (d) PEF (peak expiratory flow in liters per minute) measured daily in the morning and evening in the subset of patients capable of performing PEF testing; (e) changes in health status measurements, including the Modified Functional Status II Scale Child Health Status Scale and the RAND General Health Index; and (f) differences in asthma-related health care utilization and indirect health care costs.

Safety Variables

Safety variables were: (a) reported adverse effects that could be due to the drug; (b) morning basal and post-ACTH-simulation effects on plasma cortisol levels (HPA-axis function); and (c) changes in physical examinations, vital signs, and clinical laboratory tests, including oropharyngeal and nasal fungal cultures.

Statistical Methods

Analysis of variance was used to compare differences between treatment groups for all efficacy variables, with the exception of patient outcomes, which were analyzed using Fisher's exact test. Analysis of variance was also used for morning basal and post-ACTH-simulation effects on plasma cortisol levels. Descriptive statistics were used to present all other safety data.

Efficacy Results

Results of nighttime and daytime asthma symptom scores, and the number of days of use of breakthrough medication are presented in Table 1. Data are expressed as the adjusted mean change from baseline over the 12-week treatment phase, all patients treated, last value carried forward (*$p \leq 0.050$, $p \leq 0.010$, and *$p \leq 0.001$ versus placebo (PBO); "n" is number of patients). Thus improvements are indicated by negative values of these variables. Patients in the 0.25 mg, 0.5 mg, and 1.0 mg per day treatment groups showed statistically significant improvements in their asthma symptom scores and fewer days of bronchodilator therapy when compared to placebo.

The total proportion of patients who were discontinued from the placebo group (28%) was greater than that for the budesonide groups (19%, 24%, and 14% for the 0.25 mg, 0.5 mg and 1.0 mg groups, respectively); the proportion in the placebo group was significantly different from that in the 1 mg group (p=0.020). The proportion of patients in the placebo group discontinuing due to worsening asthma (23%) was also greater than for the budesonide groups (14%, 17% and 13% of patients in the 0.25 mg, 0.5 mg and 1.0 mg groups, respectively). These differences were not statistically significant. Since the study was double-blind, patients with worsening asthma in all study groups were discontinued in order to ensure that the placebo patients with worsening asthma could receive alternate therapy.

TABLE 1

Comparison of the Efficacy of Three Different Doses of Budesonide

| | | Budesonide Dose | | |
|---|---|---|---|---|
| Variable Asthma scores: | PBO (n = 92) | 0.25 mg (n = 91) | 0.5 mg (n = 82) | 1.0 mg (n = 93) |
| Nighttime | −0.16 | −0.49*** | −0.42** | −0.42** |
| Daytime | −0.26 | −0.57** | −0.46* | −0.50* |
| Days of use of bronchodilator | −4.19 | −6.26* | −5.31* | −5.98* |
| $FEV_1$ (L) | −0.07 | −0.01 | 0.03* | 0.03* |
| | (n = 38) | (n = 29) | (n = 28) | (n = 33) |
| Morning PEF (L/min) | 7.1 | 14.4 | 6.5 | 10.9 |
| | (n = 55) | (n = 44) | (n = 41) | (n = 55) |

Improvements in lung function were associated with budesonide treatment in the subset of patients capable of performing PFT (Table 1). Clinically and statistically significant improvements in $FEV_1$ were observed in the 0.5 mg and 1.0 mg budesonide treatment groups compared to placebo. Improvements in FVC, $FEF_{25-75}$ and morning and evening PEF were also observed in the budesonide groups, with FVC improvements in the 0.5 mg treatment group being statistically significant compared to placebo.

Patients in the 0.25 mg budesonide treatment group had clinically and statistically significant improvements compared to placebo in health status scores at weeks 4 and 12 for the FS-II(R) General score. Improvements were also seen in the FS-II(R) Specific scores, with statistical significance compared to placebo for the 0.5 mg budesonide group at week 12. Patients in all the budesonide treatment groups also demonstrated improvements in the RAND General Health Index scores compared to placebo. In addition, patients in the budesonide treatment groups showed improvements in health care utilization and fewer asthma-related phone calls to physicians. Variables associated with indirect costs, including days absent from school, and days in which routine was interrupted also showed improvement.

Safety Results

There were no deaths reported during the study. There were a total of 10 serious adverse events in 8 of the patients in the study. There were 4 discontinuations due to adverse events.

This study showed that children aged between six months and eight years with asthma, receiving budesonide at the three doses once a day for 12 weeks, had no clinically relevant differences in the frequency of clinically significant changes in nasal or oral fungal cultures between treatment groups. There were no clinically relevant differences between treatment groups in vital signs or physical examination differences.

Assessments to determine the possible effects of study treatment on basal and post-ACTH-stimulated plasma cortisol levels showed no significant differences between active treatment groups and placebo from baseline to week 12. Thus, there was no evidence of HPA-axis suppression by budesonide at the three doses studied. ACTH production is stimulated by injection (intravenous for young children and intramuscular for infants) of corticotropin one hour before morning blood sampling.

Conclusion

This study in infants and young children aged six months to eight years with asthma demonstrated that the budesonide containing suspension significantly improved both nighttime and daytime asthma symptoms compared to placebo. Efficacy was further supported by a decrease in the use of short-acting bronchodilators and by an increase in $FEV_1$ (in the subgroup of patients who could consistently perform spirometry). Furthermore, there were no differences between treatments in spontaneously reported adverse events or response to ACTH-stimulation tests, strongly supporting the safety of 0.25 mg to 1.0 mg budesonide containing suspension administered once per day. All three doses of budesonide in suspension were more efficacious than placebo, but there were no differences between the three active treatments.

In summary, budesonide in a nebulized suspension, administered at 0.25 mg, 0.5 mg, or 1.0 mg once daily, is an effective and well-tolerated treatment for non-steroid-treated infants and young children between six months and eight years of age.

Example 2

A Phase III Study of Four Dose Regimens of Budesonide in a Nebulizing Suspension and Placebo in Asthmatic Children Aged Eight Years and Younger Objectives The objectives of the study were to compare the relative efficacy and safety of budesonide in a nebulizing suspension (0.25 mg administered once a day (QD), 0.25 mg administered twice per day (BID), 0.5 mg BID or 1.0 mg QD) in pediatric asthmatic patients aged six months to eight years.

Methodology

This was a multicenter, randomized double-blind, placebo-controlled, parallel-group study.

Number of Subjects

The number of patients in the study was 481, the number analyzed for efficacy was 471, and the number analyzed for safety was 480.

Diagnoses and Main Criteria for Inclusion

Patients were mild to moderate asthmatic children aged six months to eight years of age with a diagnosis of asthma as defined by the National Institutes of Health of the U.S. Department of Health and Human Services, including: (a) exacerbations of cough and/or wheezing on a frequent basis, including nocturnal asthma, with infrequent severe exacerbations during the last six months; (b) daily use of at least one chronic asthma medication (which could have been an inhaled GCS) with periodic use of breakthrough medication for at least three months prior to Visit 1; and (c) basal $FEV_1$ of $\geq 50\%$ of predicted and reversibility of $\geq 15\%$ at $15\pm 5$ minutes after a standard dose of inhaled bronchodilator for patients capable of performing consistent PFTs.

Test Drug, Doses and Mode of Administration

Budesonide was administered once per day as a nebulized suspension, at the indicated doses (0.25 mg QD, 0.25 mg BID, 0.5 mg BID or 1.0 mg QD) by the mode described in Example 1.

Efficacy Variables

Primary efficacy variables were mean changes from baseline in daytime and nighttime asthma symptom scores over the 12-week treatment phase. The symptom scores were obtained as in Example 1.

Secondary efficacy variables were: (a) the number of days breakthrough (bronchodilator) medication was used; (b) spirometry test variables, including $FEV_1$, $FEF_{25-75}$, and FVC performed at clinic visits in the subset of patients capable of performing spirometry testing; (c) PEF measured daily in the morning and evening in the subset of patients capable of performing PEFs; and (d) proportion of patient discontinuations from the study.

Safety Variables

Safety variables were: (a) reported adverse events that could be due to the drug; (b) morning basal and post-ACTH-simulation effects on plasma cortisol levels (HPA-axis function) in a subset of patients; and (c) changes in physical examinations, vital signs and clinical laboratory tests, including oropharyngeal and nasal fungal cultures.

Statistical Methods

Analysis of variance was used to compare differences between treatment groups for all efficacy variables, with the exception of patient discontinuations from the study, which was analyzed using Fisher's exact test. Analysis of variance was also used for morning basal and post-ACTH-simulation effects on plasma cortisol levels. Descriptive statistics were used to present all other safety data.

Efficacy Results

A total of 481 patients were included in the study. Patient demographies were similar for the four treatment groups. Males constituted 64.4% of the randomized patients. 80.5% of the patients were Caucasian, with the rest being Blacks (13.7%), Hispanics (3.7%), and other ethnic groups (2.1%). The mean age, weight, and height at screening were $55\pm 26.3$ months (range 7–108 months), $43.1\pm 16.3$ pounds ($19.5\pm 7.4$ kg) and $106.5\pm 16.4$ cm, respectively. The mean duration of asthma at screening was $34.2\pm 22.9$ months. The mean nighttime and daytime asthma symptom scores at baseline were $1.22\pm 0.62$ and $1.28\pm 0.50$, respectively. A total of 164 (34.1%) of the patients were capable of performing PEF maneuvers. The mean morning and evening PEF values at baseline for these patients were $159.9\pm 43.0$ and $168.3\pm 43.1$ L/min, respectively.

A total of 471 patients were evaluated for efficacy (all patients treated). Efficacy results are shown in Table 2. Data are expressed as the adjusted mean change from baseline over the 12-week treatment phase, all patients treated, last value carried forward ($*p \leq 0.050$; $p \leq 0.010$ and $*p \leq 0.001$, versus placebo; "n" is the number of patients).

TABLE 2

COMPARISON OF THE EFFICACY OF BUDESONIDE ADMINISTERED ONCE AND TWICE PER DAY

| | | Budesonide Dose | | | |
| --- | --- | --- | --- | --- | --- |
| | Placebo | 0.25 mg QD | 0.25 mg BID | 0.5 mg BID | 1.0 mg QD |
| Nighttime Asthma Symptom Score | −0.13 (n = 92) | −0.28 (n = 93) | −0.49*** (n = 97) | −0.42** (n = 96) | −0.40** (n = 93) |
| Daytime Asthma Symptom Score | −0.19 (n = 92) | −0.28 (n = 92) | −0.40* (n = 97) | −0.46** (n = 96) | −0.37* (n = 93) |
| Number of Days Use of Breakthrough Medication | −2.36 (n = 92) | −4.39* (n = 93) | −5.22*** (n = 97) | −4.92** (n = 96) | −4.38* (n = 93) |

TABLE 2-continued

COMPARISON OF THE EFFICACY OF BUDESONIDE
ADMINISTERED ONCE AND TWICE PER DAY

|  | | Budesonide Dose | | | |
| --- | --- | --- | --- | --- | --- |
|  | Placebo | 0.25 mg QD | 0.25 mg BID | 0.5 mg BID | 1.0 mg QD |
| Morning PEF | −0.2 (n = 32) | 10.9 (n = 32) | 23.0** (n = 34) | 24.8** (n = 29) | 17.1* (n = 34) |
| Evening PEF | 1.9 (n = 32) | 16.8* (n = 32) | 19.2* (n = 34) | 21.0** (n = 29) | 14.1 (n = 34) |
| $FEV_1$ | 0.04 (n = 28) | 0.07 (n = 31) | 0.03 (n = 33) | 0.17* (n = 29) | 0.11 (n = 34) |

The data demonstrated that 0.25 mg BID, 0.5 mg BID, and 1.0 mg QD budesonide provided statistically significant and clinically relevant improvement in patient nighttime and daytime asthma symptoms compared to placebo. Furthermore, patients receiving all four budesonide regimens had statistically significant and clinically relevant decreases in the number of days of breakthrough medication use compared to placebo.

In those children who could perform PEF assessments, statistically significant improvements in morning PEF from baseline to weeks 0–12 were seen in the 0.25 mg BID, 0.5 mg BID, and 1.0 mg QD mg budesonide treatment groups compared to placebo. Statistically significant improvements in evening PEF from baseline to weeks 0–12 were seen in the 0.25 mg QD, 0.25 mg BID, and 0.5 mg QD budesonide nebulizing suspension treatment groups compared to placebo. In those patients able to perform PFTs consistently, the lung function measures of FEVI, FVC, and $FEF_{25-75}$ improved clinically for all the budesonide treatment groups compared to placebo, with statistical significance achieved in $FEV_1$ and FVC for the budesonide 0.5 mg BID treatment group.

The total proportion of patients who were discontinued from the placebo group (39%) was greater than that for the budesonide treatment groups (21%, 21%, 19% and 31% for the 0.25 mg QD, 0.25 mg BID, 0.5 mg BID and 1.0 mg QD groups, respectively); the proportion in the placebo group was significantly different from those in the 0.25 mg QD, 0.25 mg BID, and 0.5 mg BID budesonide treatment groups (p<0.01). The proportion of patients in the placebo group discontinuing due to worsening asthma (26.3%) was also greater than for budesonide treatment groups (16.0%, 13.1%, 15.3% and 21.1% of patients for the 0.25 mg QD, 0.25 mg BID, 0.5 mg BID, and 1.0 mg QD groups, respectively; these differences were statistically significant for the 0.25 mg BID budesonide versus placebo comparison, p=0.029).

Safety Results

One randomized patient never took the study drug and therefore was not included in the safety analysis. There were no deaths reported during the study. A total of 13 serious adverse events in 13 patients were reported during the treatment phase, all recovering completely without sequelae (4, 4, 2, 1, and 4 serious adverse events in the placebo, 0.25 mg QD, 0.25 mg BID, 0.5 mg BID, and 1.0 mg QD groups, respectively). A total of six patients were discontinued due to adverse effects (2, 1, 1, and 2 patients in the placebo and the 0.25 mg BID, 0.5 mg BID, and 1.0 mg QD groups, respectively). One of the adverse events leading to discontinuation from the treatment phase was judged by the investigator to be of probable relationship to the study treatment. The patient was in the 1.0 mg QD group and developed laryngismus.

The study showed that children aged six months to eight years with asthma, receiving budesonide as a nebulized suspension at 0.25 mg QD, 0.25 mg BID, 0.5 mg BID, or 1.0 mg QD for 12 weeks had no clinically relevant differences in the type, incidence or severity of adverse events compared to placebo. There were also no apparent differences in the number of patients with clinically significant changes in nasal or oral fungal cultures between treatment groups. There were no clinically relevant differences between treatment groups in vital signs or physical examination outcomes.

Assessments to determine the possible effects of study treatment on basal and post-ACTH-stimulated plasma cortisol levels showed no significant differences between the active treatment groups and placebo from baseline to week 12. Thus, there was no evidence of HPA-axis suppression by budesonide in a nebulized suspension when administered in the four regimens studied.

Conclusion

Budesonide in a nebulized suspension, when administered in regimens of 0.25 mg QD, 0.25 mg BID, 0.5 mg BID, or 1.0 mg QD, was effective and well tolerated by infants and young children aged between six months and eight years with asthma who had previously been or not been treated with inhaled GCS.

OTHER EMBODIMENTS

It is understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a patient suffering from a respiratory disease, the method comprising administering to the patient a nebulized dose of a budesonide composition in a continuing regimen at a frequency of not more than once per day, wherein the administration is in the evening.

2. The method of claim 1, wherein the frequency is once and only once per day.

3. The method of claim 1, wherein the frequency is once and only once every other day.

4. The method of claim 1, wherein the respiratory disease is selected from the group consisting of an inflammatory airway disease, croup, and bronchopulmonary dysplasia.

5. The method of claim 4, wherein the respiratory disease is asthma.

6. The method of claim 4, wherein the respiratory disease is chronic obstructive pulmonary disease or bronchiolitis.

7. The method of claim 1, wherein the patient is one day to fifteen years old.

8. The method of claim 1, wherein the patient is one month to eight years old.

9. The method of claim 1, wherein the patient is six months to five years old.

10. The method of claim 1, wherein the budesonide composition contains 0.05 mg to 15 mg budesonide.

11. The method of claim 10, wherein the budesonide composition further comprises water and 0.05 mg to 0.15 mg sodium edetate, 8.0 mg to 9.0 mg sodium chloride, 0.15 mg to 0.25 mg polysorbate, 0.25 mg to 0.30 mg anhydrous citric acid, and 0.45 mg to 0.55 mg sodium citrate per 1 ml of water.

12. The method of claim 1, wherein the budesonide composition contains 0.1 mg to 2.0 mg budesonide.

13. The method of claim 1, wherein the budesonide composition contains 0.25 mg to 1.0 mg budesonide.

14. The method of claim 1, wherein the budesonide composition is a suspension.

15. The method of claim 1, wherein the budesonide composition is a solution.

16. The method of claim 1, wherein budesonide is the only active ingredient in the budesonide composition.

17. A kit for treating a respiratory disease, the kit comprising (a) a budesonide suspension in a sealed container, the suspension containing 0.05 mg to 15 mg budesonide and a solvent, and (b) a label indicating administration by nebulization in a continuing regimen at a frequency of not more than once per day.

18. The kit of claim 17, wherein the frequency is once and only once per day.

19. The kit of claim 17, wherein the frequency is once and only once every other day.

20. The kit of claim 17, wherein the respiratory disease is selected from the group consisting of an inflammatory airway disease, croup, and bronchopulmonary dysplasia.

21. The kit of claim 20, wherein the respiratory disease is asthma.

22. The kit of claim 20, wherein the respiratory disease is chronic obstructive pulmonary disease or bronchiolitis.

23. The kit of claim 17, wherein the administration is in the evening.

24. The kit of claim 17, wherein the patient is one day to fifteen years old.

25. The kit of claim 17, wherein the patient is one month to eight years old.

26. The kit of claim 17, wherein the patient is six months to five years old.

27. The kit of claim 17, wherein budesonide is the sole active ingredient in the composition.

* * * * *

UNITED STATES PATENT AND TRADEMARK OFFICE
CERTIFICATE OF CORRECTION

PATENT NO. : 6,899,099 B2
DATED : May 31, 2005
INVENTOR(S) : Bertil Andersson, Goran Eriksson and Thor-Bjorn Conradsson It is certified that error appears in the above-identified patent and that said Letters Patent is hereby corrected as shown below:

Title page,
Item [22], PCT Filed: should read -- April 8, 2003 --.
Item [56], References Cited, U.S. PATENT DOCUMENTS, "5,906,202" reference, "Schuster" should be -- Shuster --.
OTHER PUBLICATIONS, "Reijonen et al." reference, "Branchiolitis" should be -- Bronchiolitis --.

Signed and Sealed this

First Day of November, 2005

JON W. DUDAS
*Director of the United States Patent and Trademark Office*